United States Patent [19]

Zhong

[11] Patent Number: 5,702,754
[45] Date of Patent: Dec. 30, 1997

[54] METHOD OF PROVIDING A SUBSTRATE WITH A HYDROPHILIC COATING AND SUBSTRATES, PARTICULARLY MEDICAL DEVICES, PROVIDED WITH SUCH COATINGS

[75] Inventor: Sheng-Ping Zhong, Farum, Denmark

[73] Assignee: Meadox Medicals, Inc., Oakland, N.J.

[21] Appl. No.: 392,141

[22] Filed: Feb. 22, 1995

[51] Int. Cl.⁶ .............. B05D 1/36; B05D 3/02; B05D 5/08; B05D 7/02
[52] U.S. Cl. .............. 427/2.12; 427/2.28; 427/2.3; 427/333; 427/302
[58] Field of Search .............. 427/2.3, 2.28, 427/302, 333, 340, 2.12

[56] References Cited

U.S. PATENT DOCUMENTS

| | | | |
|---|---|---|---|
| 3,663,288 | 5/1972 | Miller | 117/7 |
| 3,779,792 | 12/1973 | Stoy et al. | 427/407.2 |
| 4,047,957 | 9/1977 | De Winter et al. | 96/67 |
| 4,100,309 | 7/1978 | Micklus et al. | 427/2 |
| 4,119,094 | 10/1978 | Micklus et al. | 128/132 |
| 4,263,188 | 4/1981 | Hampton et al. | 427/128 |
| 4,306,998 | 12/1981 | Wenzel et al. | 260/13 |
| 4,373,009 | 2/1983 | Winn | 428/424.2 |
| 4,387,024 | 6/1983 | Kurihara et al. | 427/245 |
| 4,459,317 | 7/1984 | Lambert | 427/2 |
| 4,536,175 | 8/1985 | Anderson et al. | 604/266 |
| 4,548,844 | 10/1985 | Podell et al. | 428/35 |
| 4,642,267 | 2/1987 | Creasy et al. | |
| 4,666,437 | 5/1987 | Lambert | 427/2.3 |
| 4,675,361 | 6/1987 | Ward, Jr. | 525/92 |
| 4,692,352 | 9/1987 | Huddleston | 427/208.4 |
| 4,705,709 | 11/1987 | Vailancourt | 428/36 |
| 4,721,117 | 1/1988 | Mar et al. | 128/772 |
| 4,748,986 | 6/1988 | Morrison et al. | |
| 4,833,014 | 5/1989 | Linder et al. | 427/333 |
| 4,841,976 | 6/1989 | Packard et al. | |
| 4,867,173 | 9/1989 | Leoni | 128/772 |
| 4,876,126 | 10/1989 | Takemura et al. | |
| 4,884,579 | 12/1989 | Engelson | |
| 4,925,698 | 5/1990 | Klausner et al. | 427/2 |
| 4,943,460 | 7/1990 | Markle et al. | 428/36.9 |
| 4,959,074 | 9/1990 | Halpern et al. | 623/66 |
| 4,964,409 | 10/1990 | Tremulis | 128/657 |
| 4,980,231 | 12/1990 | Baker et al. | 428/36.9 |
| 5,002,582 | 3/1991 | Guire et al. | 623/66 |
| 5,007,928 | 4/1991 | Okamura et al. | 623/6 |
| 5,008,363 | 4/1991 | Mallon et al. | 528/49 |
| 5,026,607 | 6/1991 | Kiezulas | 428/423 |
| 5,037,656 | 8/1991 | Pitt et al. | 424/443 |
| 5,037,677 | 8/1991 | Halpern et al. | 427/338 |
| 5,040,543 | 8/1991 | Badera et al. | |
| 5,049,403 | 9/1991 | Larm et al. | 427/2 |
| 5,057,371 | 10/1991 | Canty et al. | 428/411.1 |
| 5,066,705 | 11/1991 | Wickert | 524/457 |
| 5,067,489 | 11/1991 | Lind | |
| 5,069,217 | 12/1991 | Fleishacker, Jr. | |
| 5,069,226 | 12/1991 | Yamuchi et al. | |
| 5,079,093 | 1/1992 | Akashi et al. | 428/411.1 |
| 5,080,683 | 1/1992 | Šulc et al. | 623/66 |
| 5,080,924 | 1/1992 | Kamel et al. | 427/2 |
| 5,084,315 | 1/1992 | Karimi et al. | 427/2.28 |
| 5,091,205 | 2/1992 | Fan | 427/2.28 |
| 5,102,401 | 4/1992 | Lambert et al. | 604/264 |
| 5,105,010 | 4/1992 | Sundararaman et al. | 564/252 |
| 5,107,852 | 4/1992 | Davidson et al. | |
| 5,128,170 | 7/1992 | Matsuda et al. | 427/2 |
| 5,129,890 | 7/1992 | Bates et al. | |
| 5,160,790 | 11/1992 | Elton | 428/412 |
| 5,211,183 | 5/1993 | Wilson | |
| 5,213,111 | 5/1993 | Cook et al. | |
| 5,217,026 | 6/1993 | Stoy et al. | |
| 5,240,994 | 8/1993 | Brink et al. | 525/54.2 |

(List continued on next page.)

FOREIGN PATENT DOCUMENTS

| | | |
|---|---|---|
| 556350 | 9/1986 | Australia. |
| 556351 | 9/1986 | Australia. |
| 0 093 094 | 11/1983 | European Pat. Off.. |
| 0 106 004 | 4/1984 | European Pat. Off.. |
| 0 166 998 | 1/1986 | European Pat. Off.. |
| 0 389 632 | 10/1990 | European Pat. Off.. |
| 0 395 098 | 10/1990 | European Pat. Off.. |
| 0 407 965A1 | 1/1991 | European Pat. Off.. |
| 0 439 908 A1 | 8/1991 | European Pat. Off.. |
| 0 480 809 A2 | 4/1992 | European Pat. Off.. |
| 0 592 870 A1 | 9/1993 | European Pat. Off.. |
| 0 611 576 A1 | 2/1994 | European Pat. Off.. |
| 1 435 797 | 5/1976 | United Kingdom. |
| 2 128 500 | 5/1984 | United Kingdom. |
| PCT/DK/91/ 00163 | 12/1991 | WIPO. |
| PCT/US92/ 09073 | 10/1992 | WIPO. |

OTHER PUBLICATIONS

PEBAX 3533 SA 00 Base Polymer for Structural Hot Melt Adhesives (no date supplied).

*Primary Examiner*—Dana Dudash
*Attorney, Agent, or Firm*—Hoffmann & Baron, LLP

[57] ABSTRACT

A substrate such as a catheter or a guide wire is provided with a lubricous, hydrophilic abrasion-resistant coating by:

a) coating said substrate with a first aqueous coating composition comprising an aqueous dispersion or emulsion of a polymer having organic acid functional groups and a polyfunctional crosslinking agent having functional groups capable of reacting with organic acid groups, and drying the coating to obtain a substantially water-insoluble coating layer having excess polyfunctional including functional groups being reactive with organic acid groups remaining, and b) contacting the dried coating layer obtained in a) with a second aqueous coating composition comprising an aqueous solution or dispersion of a hydrophilic polymer having organic acid functional groups, and drying the combined coating, the hydrophilic polymer thereby becoming bonded to the polymer of the first coating composition through the excess crosslinking agent.

The drying can be carried out at ambient (room) temperature.

27 Claims, No Drawings

U.S. PATENT DOCUMENTS

| | | |
|---|---|---|
| 5,241,970 | 9/1993 | Johlin, Jr. et al. . |
| 5,243,996 | 9/1993 | Hall . |
| 5,250,613 | 10/1993 | Bergstrom et al. .................... 525/54.1 |
| 5,266,359 | 11/1993 | Spielvogel ........................... 427/388.4 |
| 5,272,012 | 12/1993 | Opolski ................................ 427/2.1 |
| 5,275,173 | 1/1994 | Samson et al. . |
| 5,290,585 | 3/1994 | Elton ............................................ 427/2 |
| 5,304,140 | 4/1994 | Kugo et al. . |
| 5,478,676 | 12/1995 | Turi et al. ................................ 429/234 |
| 5,576,072 | 11/1996 | Hostettler et al. ..................... 427/2.22 |
| 5,620,738 | 4/1997 | Fan et al. ................................ 427/2.3 |

METHOD OF PROVIDING A SUBSTRATE WITH A HYDROPHILIC COATING AND SUBSTRATES, PARTICULARLY MEDICAL DEVICES, PROVIDED WITH SUCH COATINGS

This invention relates to a method of providing a substrate, particularly a medical device or a part of such device intended for introduction in the human body, with a hydrophilic coating becoming lubricous when contacted with an aqueous fluid and substrates, particularly medical devices, provided with such hydrophilic coatings.

It is generally known to provide substrates like medical devices or parts of such devices with a hydrophilic coating for the purpose of reducing the friction when the device is introduced in a humid environment like the human body. Such hydrophilic coatings have also been referred to as lubricous or "slippery" coatings.

Catheters and other medical devices used for introduction in blood vessels, urethra, body conduits and the like and guide wires used with such devices are examples of medical devices which may be provided with hydrophilic coatings. Catheters for balloon angioplasty and biopsy are specific examples of such catheters.

Substrates and medical articles or devices which it may be desirable to provide with a hydrophilic coating and methods for providing such substrates and articles or devices with hydrophilic coatings have been described in an abundant number of references, examples of which are mentioned in the following.

U.S. Pat. No. 4,119,094 discloses a method of coating a substrate with a polyvinylpyrrolidone-polyurethane interpolymer. In the method, a polyisocyanate and a polyurethane in a solvent such as methyl ethyl ketone are applied to a substrate and the solvent evaporated after which polyvinylpyrrolidone in a solvent is applied to the treated substrate and the solvent evaporated.

U.S. Pat. No. 5,091,205 discloses a method of providing a substrate with a hydrophilic lubricous coating in which the substrate is first contacted with a polyisocyanate solution to provide coupling, then contacted with a poly(carboxylic acid) solution to give a coating and then finally oven-dried. Methyl ethyl ketone is the preferred solvent for the polyisocyanates and dimethyl formamide for the poly(carboxylic acid). It is mentioned that the polyisocyanates can be emulsified to form an oil-in-water emulsion in which case, however, the reactive isocyanate groups need to be protected by suitable chemical groups.

EP Patent No. 0 106 004 B1 discloses a method of forming a hydrophilic coating on a substrate by applying a coating from a solvent solution of a polyisocyanate to form a coupling coating followed by application of a solvent solution of a hydrophilic copolymer made from monomers selected from vinyl pyrrolidone, vinyl methyl ether or vinyl pyridine and a monomer containing active hydrogen which will react with isocyanate to form a covalent bond between the coupling coating and the hydrophilic copolymer.

EP Patent No. 0 166 998 B1 discloses a method for treating the surface of a medical instrument. The surface is treated with a solution of a polymer having a reactive functional group in an organic solvent followed by treatment with a water-soluble polymer selected from maleic anhydride polymers, cellulosic polymers, polyethylene oxide polymers, and water-soluble nylons or derivatives thereof to covalently bond the reactive functional group with the water-soluble polymer after which the treated substrate is optionally contacted with water.

U.S. Pat. No. 5,077,352 discloses a method in which a flexible, lubricous, organic polymeric coating is formed by applying a mixture of an isocyanate, a polyol and a poly (ethylene oxide) in a carrier liquid to a surface to be coated. The carrier liquid is removed and the mixture reacted to form a polyurethane coating with associated poly(ethylene oxide). Methylene chloride, chloroform, dichloroethane, acetonitrile, dichloroethylene, and methylene bromide are mentioned as suitable carrier liquids.

International Patent Applications Nos. PCT/EP92/00918, PCT/EP92/00919, and PCT/DK92/00132 disclose methods for providing different medical devices having a polyurethane surface with a coating of a hydrophilic poly(meth) acrylamide. Before application of the hydrophilic coating the substrate is treated with a compound having functional groups capable of reacting with the polyurethane and the poly(meth)acrylamide, respectively, typically a di or higher functionality isocyanate in an organic solvent.

A drawback of the methods according to the above-mentioned references is that the provision of the hydrophilic coating usually involves the use of organic solvents or toxic chemicals, for instance polyisocyanates, which can present environmental problems and/or health risks. In order to avoid the use of solvents some non-solvent methods have been developed.

EP Patent Application No. 92100787.8, Publication No. EP 0 496 305 A2, discloses a method for preparing a shaped medical article provided with a lubricous coating. A coating composition comprising a blend of polyurethane and polyvinylpyrrolidone is co-extruded with a substrate polymer to give a shaped article having thereon a layer of the coating composition which becomes lubricous when contacted with water.

U.S. Pat. No. 5,041,100 discloses a method for coating a substrate with a mixture of poly(ethylene oxide) and an aqueous dispersion of structural plastic material, e.g. polyurethane. As indicated in column 2, lines 15–21, the poly (ethylene oxide) is admixed without crosslinking in intimately dispersed relation with the structural plastic material to provide a hydrophilic component to the system, which may leach to the surface, or which may be entrapped adjacent the surface to provide a hydrophilic character thereto and reduce friction, particularly when hydrated.

The methods described in the above-mentioned references have the drawback that the interpolymer network physically attaching the hydrophilic polymer to the substrate often breaks down upon prolonged turbulent flow or soaking, and that the hydrophilic species can be washed away thereby rendering the article insufficiently lubricous.

Finally, International Patent Application No. PCT/DK91/ 00163 discloses a method of providing a medical instrument with a hydrophilic, low-friction coating, which method comprises the steps of forming an inner layer from an aqueous polymer emulsion and an outer layer from an aqueous solution of a water-soluble hydrophilic polymer and curing the two layers simultaneously following application of the outer layer by heating to a temperature of above 100° C.

The above method eliminates the use of organic solvents and results in a coating which is strongly attached to the substrate. However, the use of curing temperatures above 100° C. limits the use of the method, because many devices, for instance poly(ethylene terephthalate) (PET) balloon catheters cannot resist such temperatures.

The present invention is directed to a method of providing a substrate, particularly a medical device or a part of such device intended for introduction in the human body, with a hydrophilic coating becoming lubricous when contacted with an aqueous fluid, which method among others makes it possible to coat devices which are sensitive to high processing temperatures, such as (PET) balloon catheters. The hydrophilic polymer becomes covalently bonded to the polymer of the first coating.

Like the method according to PCT/DK91/00163, the method according to the invention uses aqueous coating compositions, but the method according to the present invention can be carried out at much lower temperatures, for instance at room temperature.

As a further advantage the method according to the invention results in a very abrasion-resistant coating.

The method according to the invention comprises a) coating a substrate with a first aqueous coating composition comprising an aqueous dispersion or emulsion of a polymer having organic acid functional groups and a polyfunctional crosslinking agent having functional groups being capable of reacting with organic acid groups, and drying the coating to obtain a substantially water-insoluble coating layer still including functional groups being reactive with organic acid groups, and b) contacting the dried coating layer obtained in a) with a second aqueous coating composition comprising an aqueous solution or dispersion of a hydrophilic polymer having organic acid functional groups, and drying the combined coating, the hydrophilic polymer thereby becoming bonded to the polymer of the first coating composition through the crosslinking agent.

Included as an aspect of the present invention is a medical device intended for introduction to the body comprising a substrate suitable for introduction into the body, the surface of said substrate being coated with a cured polymeric composition, said composition comprising a first polymeric layer formed from at least a partial reaction of an aqueous dispersion or emulsion of a polymer having reactive organic acid functional groups present with a polyfunctional crosslinking agent capable of reacting with said organic acid functional groups, and a second hydrophilic polymeric layer having organic acid functional groups present and being capable of reacting with said crosslinking agent. As described further herein, the first polymeric layer is substantially cross-linked prior to the application of the second polymeric layer. Sufficient functional groups remain from the crosslinking agent to participate in covalent bonding with the second polymeric layer. This covalent bonding allows for excellent adhesion of the lubricous, hydrophilic layer to the first polymeric coating. The coating has excellent wear resistance, lubricity and can be applied in extremely thin layers so as not to affect the mechanical properties of the substrate to which it is applied. This is particularly important when the coating is to be applied to a thin-walled inflatable balloon on a balloon catheter used for angioplasty.

Also contemplated as part of the present invention is a reactive film coating useful for bonding hydrophilic polymers having organic acid functional groups present, said film coating being the reaction product of an aqueous dispersion or emulsion of a polymer having organic acid functional groups and a polyfunctional crosslinking agent capable of reacting with said organic acid functional groups, whereby said reaction product still includes reactive functional groups from said polyfunctional crosslinking agent. This aspect of the invention is intended to cover that portion of the coating prior to further reaction with the hydrophilic, second coating which is applied to obtain lubricity. Thus, articles which have been coated only with the first coating and are prepared for the application of a hydrophilic coating capable of imparting lubricity when in contact with water is covered in this embodiment.

A further aspect of the present invention includes a hydrophilic polymeric coating capable of become lubricous when in contact with an aqueous medium, said coating including at least two polymeric layers covalently bonded together to form a cross-linked network, said cross-linked network being the reaction product of:

a) a first polymeric layer comprising an aqueous dispersion or emulsion of a polymer having organic acid functional groups and a polyfunctional crosslinking agent capable of reacting with said organic acid functional groups; and b) a second aqueous polymeric layer comprising an aqueous solution or dispersion of a hydrophilic polymer having organic acid functional groups. The hydrophilic polymer coating of the first polymeric layer may be selected from any number of polymers recited herein. Of particular preference, however, are the water-borne polyurethane polymers and polyacrylic acid polymers. The second polymeric layer may also be selected from a wide variety of polymers which can be covalently bonded to the first coating layer due to the presence of their organic acid functionality. Of particular preference are the polyacrylic acid polymers and the acrylamide-acrylic acid copolymers.

As previously mentioned, medical devices which are at least partially coated with the coatings of the present invention have particular advantages over the prior art in that they can easily be inserted into the body with less frictional resistance due to the lubricous characteristics of the outer coating. Additionally, the adherence of the outer coating is improved over the prior art due to the covalent bonding which occurs between the two coating layers. As mentioned herein, the coating of angioplasty inflatable balloons which are an integral part of angioplasty balloon catheters is one specific application intended for the coatings of the present invention. Additionally, other medical devices such as guide wires and the like are contemplated. The devices need not necessarily be intended for use inside the body, and exterior uses are also contemplated.

The present invention also contemplates a kit which includes as a first component an aqueous dispersion of a polymer having organic acid functionality, as a second component a polyfunctional crosslinking agent being reactive with said organic acid functionality of the first component and as a third component an aqueous solution or dispersion of a hydrophilic polymer having organic acid functionality and which when cured and placed in contact with water imparts lubricity.

In the present context the term "organic acid group" is meant to include any groupings which contain an organic acidic ionizable hydrogen. Examples of functional groupings which contain organic acidic ionizable hydrogen are the carboxylic and sulfonic acid groups. The expression "organic acid functional groups" is meant to include any groups which function in a similar manner to organic acid groups under the reaction conditions, for instance metal salts of such acid groups, particularly alkali metal salts like lithium, sodium and potassium salts, and alkaline earth metal salts like calcium or magnesium salts, and quaternary amine salts of such acid groups, particularly quaternary ammonium salts.

The polymer having organic acid functional groups, which is included in the first aqueous coating composition, will be selected duly paying regard to the nature of the substrate to be coated. Typically the polymer in the first coating composition will be selected from homo- and copolymers including vinylic monomer units, polyurethanes, epoxy resins and combinations thereof. The polymer in the first coating composition is preferably selected from polyurethanes, polyacrylates, polymethacrylates, polyisocrotonates, epoxy resins, acrylate-urethane copolymers and combinations thereof having organic acid functional groups. In a particularly preferred embodiment of the method according to the invention the polymer in the first coating composition is selected from homo- and copolymers having a substantial amount of organic acid functional groups in their structure, which may act as an internal emulsifier. A specific class of polyurethanes which may be used in the first coating composition are the so-called water-borne polyurethanes, among which are the so-called internally emulsified water-borne polyurethane containing carboxylic acid groups and/or sulfonic acid groups, optionally as salts of such groups, as internal emulsifiers are particularly preferred.

Examples of water-borne polyurethanes are those supplied: under the tradename NeoRez by Zeneca Resins, for instance NeoRez-940, NeoRez-972, NeoRez-976 and NeoRez-981; under the tradename Sancure by Sanncor, for instance Sancure 2026, Sancure 2710, Sancure 1601 and Sancure 899; under the tradenames U21 and U21X by B. F. Goodrich; and under the tradenames Bayhydrol LS-2033, Bayhydrol LS-2100, Bayhydrol LS-2952 and Bayhydrol LS-2990 by Bayer AG.

Another specific class of polymers which have shown particularly useful in the first coating composition are acrylate-urethane copolymers, for instance the acrylic urethane copolymer dispersions supplied under the tradenames NeoPac E-106, NeoPac E-121, NeoPac E-130 and NeoRez R-973 by Zeneca Resins.

The concentration of the polymer in the first coating composition is usually from about 2 to about 60% by weight and preferably from about 5 to about 40% by weight calculated as solids of polymer compared to the total weight of the first coating composition.

In addition to one or more polymers having organic acid functional groups, the first aqueous coating composition comprises one or more polyfunctional crosslinking agents having functional groups being capable of reacting with organic acid groups. Polyfunctional crosslinking agents having functional groups being capable of reacting with organic acid groups are known in the art. For instance such polyfunctional crosslinking agents have been used for external crosslinking of polyurethanes.

Particularly preferred polyfunctional crosslinking agents for use in the method according to the invention are polyfunctional aziridines and polyfunctional carbodimides.

Polyfunctional aziridines and polyfunctional carbodimides and their use as crosslinking agents are known in the art.

The crosslinking agent supplied by Zeneca Resins under the tradename NeoCryl CX 100 and the crosslinking agent supplied by EIT Industries under the tradename XAMA-7 are specific examples of polyfunctional aziridine crosslinking agents which may be used in the method according to the invention, and the crosslinking agent supplied by Union Carbide under the tradename Ucarlink XL-29SE is a specific example of a polyfunctional carbodimide crosslinking agent which may be used in the method according to the invention.

Among the polyfunctional aziridines useful include the trifunctional aziridine of the following formula:

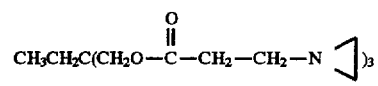

The polyfunctional crosslinking agent is preferably a crosslinking agent having more than two functional groups per molecule. Furthermore, it should be noted that a combination of polyfunctional crosslinking agents may be used in the method according to the invention.

The functional groups on the crosslinking agent serves at least two purposes. The first purpose is to crosslink the first polymeric coating. The second purpose is to participate in covalent bonding with the organic acid groups present in the second (hydrophilic) polymeric coating. As such, there must be sufficient functionality in the crosslinking agent to accomplish both purposes. That is, the amount of crosslinking agent used must be sufficient such that enough functional groups are present to substantially crosslink the first polymeric coating so that enough unreacted functional groups remain to covalently bond to the second hydrophilic layer.

One indication that insufficient functionals from the crosslinking agent are present is the inadequate bonding of the second layer. This is evidenced by the lack of wear resistance and such coatings can be easily wiped off the substrate to which they are applied.

The concentration of the crosslinking agent in the first coating composition is usually in the range from about 0.2 to about 30% by weight and preferably in the range from about 0.5 to about 20% by weight.

As is known in the art the first aqueous coating composition may include other conventional additives like levelling agents, various stabilizers, pH adjustment agents, defoaming agents, cosolvents, etc. if compatible with the intended use of the coated substrate.

The coating of the first aqueous coating composition is dried so as to obtain a substantially water-insoluble coating layer still including functional groups being reactive with organic acid groups. Hereafter, the obtained dried coating is contacted with a second aqueous coating composition comprising an aqueous solution or dispersion of a hydrophilic polymer having organic acid functional groups, after which the second coating is dried, the hydrophilic polymer thereby becoming bonded to the polymer of the first coating composition through the crosslinking agent.

Hydrophilic polymers for use in hydrophilic lubricous coatings are known in the art. In the method according to the invention any hydrophilic polymer (homo- or copolymer or mixture of one or more of such polymers) may be used provided that it contains organic acid functional groups in its structure which can react with the polyfunctional crosslinking agent having functional groups being capable of reacting with organic acid groups to form a hydrophilic coating becoming lubricous when contacted with an aqueous fluid.

The hydrophilic polymer may comprise monomer units from one or more monomers having organic acid functional groups. Preferred examples of such monomers include acrylic acid, methacrylic acid and isocrotonic acid.

In addition to comprising monomer units from at least one monomer having organic acid functional groups, the hydrophilic polymer may contain monomer units from at least one hydrophilic monomer without any organic acid functional groups, such as vinylpyrrolidone and acrylamide. A preferred example of a copolymer for use in or as the hydrophilic polymer in the method according to the present invention is an acrylic acid-acrylamide copolymer. The acrylamide-acrylic acid copolymer supplied by Allied Colloids under the tradename Versicol WN 33 is a specific example of such a copolymer.

The ability to become lubricous when hydrated is a critical aspect of the present invention. The degree of lubricity produced upon contact with aqueous medium will depend on a number of factors, including the type of hydrophilic polymer, its molecular weight, the exposure level to the aqueous medium, as well as the presence of agents which facilitate wetting. Among these, the molecular weight is the most important. The molecular weight range useful in the present invention will depend on the particular type of polymer chosen. The molecular weight of the hydrophilic polymer in the second coating composition will typically be in the range from about 100,000 to about 15 million, particularly from about 150,000 to about 10 million. Hydrophilic polymers having a molecular weight in the range from about 400,000 to about 10 million and particularly of approximately 7.5 million have been found particularly suitable for use in the method according to the invention. The aforementioned acrylamide-acrylic acid copolymer falls within this preferred molecular weight.

The concentration of the hydrophilic polymer in the second coating composition will typically be from about 0.1 to 5% by weight, preferably from about 0.5 to about 3% by weight, calculated as solids of hydrophilic polymer compared to the total weight of the second coating composition.

In a preferred embodiment of the method according to the invention the functional groups of the crosslinking agent are capable of reacting with the organic acid functional groups of the polymer in the first coating composition and the organic acid functional groups of the hydrophilic polymer at a temperature below 120° C. and preferably at a temperature below 100° C. The drying step for the second coating can be carried out at a temperature below 120° C. and preferably at a temperature below 100° C., although of course higher drying temperatures could be used if desired and compatible with the nature of the substrate to be coated. For instance a metal substrate could be dried at a higher temperature.

However, the present invention is designed with the specific intent of being effective at relatively low temperatures and particularly at ambient or room temperature, to allow for use with heat sensitive substrates. In a further preferred embodiment of the method according to the invention the functional groups of the crosslinking agent are capable of reacting with the organic acid functional groups of the polymer in the first coating composition and the organic acid functional groups of the second coating (hydrophilic polymer) at a temperature in the range of 10°–70° C., preferably at a temperature in the range of 15°–35° C. Such reactivity of the crosslinking agent makes it possible to coat the substrate at a temperature in the range of 10°–70° C. and preferably at a temperature in the range of 15°–35° C., such as at room temperature, although of course higher drying temperatures can be used, if desired.

The drying time will depend on the drying temperature, higher drying temperatures requiring shorter drying time and vice versa. However, it will be within the ordinary skill of a person skilled in the art to determine a suitable combination of drying temperatures and drying time for a specific coating.

In many cases drying at about room temperature for about 12 hours will be adequate.

Furthermore, it should be noticed that the functional groups of the crosslinking agent do not necessarily have to have the same reactivity towards the organic acid functional groups of the hydrophilic polymer and the organic acid functional groups of the first coating composition and that the drying conditions in a) and b), respectively, will be selected duly paying regard to said reactivities.

The method according to the invention can be used for the coating of many different kinds of substrates. One field of use of particular interest is the coating of medical articles for use in or on the body, particularly catheters, guide wires or parts of such articles.

Balloon catheters, and particularly balloon catheters for percutaneous angioplasty are delicate articles which have proven difficult to coat by known methods. An important part of a balloon catheter is the inflatable balloon which in a balloon catheter for percutaneous angioplasty can have a very thin wall thickness, i.e. on the order of about 20 µm. In the condition in which the balloon catheter is introduced into a blood vessel the balloon is folded up into a multilayer construction. Therefore it is of great importance that a hydrophilic coating applied to the wall of such balloon minimize the increase in the wall thickness of the balloon. Furthermore, it is important that the balloon is made of a material which can be processed into a balloon of small wall thickness, still maintaining adequate strength and furthermore having the necessary biocompatibility. Polyethylene therephthalate (PET) possesses this combination of properties, but has been difficult to coat with a hydrophilic coating. However, in accordance with the present invention it has been disclosed that a PET balloon having a wall thickness of as small as about 20 µm, can be effectively coated with a hydrophilic coating having a thickness of about 2–3 µm without damaging the balloon, and provides the required lubricity. The present invention accomplishes this because the process can be carried out using aqueous coating compositions, as opposed to organic solvent based systems and drying takes place under mild conditions, e.g. simple air drying of the coating at room temperature. For instance, as previously mentioned the drying of the combined coatings can be carried out at room temperature for about 12 to about 24 hours.

However, as previously mentioned the method according to the invention can be used for the coating of many different substrates including substrates selected from polymeric substrates, non-polymeric substrates and combinations thereof.

For example, among the useful polymeric substrates include those selected from the group consisting of olefin polymers, particularly polyethylene, polypropylene, polyvinylchloride, polytetrafluoroethylene (PTFE), polyvinylacetate, and polystyrene; polyesters, particularly poly(ethylene terephthalate); polyurethanes; polyureas; silicone rubbers; polyamides, particularly nylons; polycarbonates; polyaldehydes; natural rubbers; polyether-ester copolymers; and styrene-butadiene copolymers. This list is, of course, non-limiting.

In particular, the polymeric substrate can be selected from the group consisting of poly(ethylene terephthalate), polyurethanes, polyethylene, nylon 6, nylon 11 and polyether-ester copolymers.

Examples of useful non-polymeric substrate include those selected from the group consisting of ceramics, metals, glasses and the like.

Also, combinations of polymeric substrates and non-polymeric substrates as well as combinations of one or more polymeric substrates and/or one or more non-polymeric substrates can be coated by the method according to the invention.

The invention also relates to a coated substrate as obtainable by the method according to the invention and a medical device, particularly a catheter or a guide wire provided with a coating as obtainable by the method according to the invention.

A particularly preferred medical device according to the invention is a balloon catheter for percutaneous angioplasty having at least the balloon part provided with such coating.

The invention will be further illustrated in the following non-limiting examples representing presently preferred embodiments of the invention.

EXAMPLE 1

A first coating composition was prepared by adding the following ingredients successively to a glass beaker under proper agitation until thoroughly mixed.

| | |
|---|---|
| NeoRez R981: | 250 ml |
| Water: | 250 ml |
| 0.5% Fluorad FC-129 stock solution: (prepared by diluting 1 ml Fluorad FC-129 in 100 ml of water) | 10 ml |
| 34% NH$_4$OH: | 4 ml |
| NeoCryl CX 100: | 20 ml |

NeoRez R981 (from Zeneca Resins) is a polyester-based, aliphatic water-borne polyurethane containing carboxylic acid groups as internal emulsifier, which is stabilized by triethylamine (TEA) and has a solids content of 32% and a pH of 7.5-9.0 at 25° C. It contains a 5.3% N-methylpyrrolidone as cosolvent. NeoCryl CX 100 (from Zeneca Resins) is a polyfunctional aziridine crosslinking agent. Fluorad FC-129 (from 3M) is added as a levelling agent. Ammonium hydroxide is used to adjust the pH of the solution.

A second coating composition, as follows, was prepared:

| | |
|---|---|
| 1.2% aqueous solution of Versicol WN23: | 400 ml |

The above solution was prepared by adding an appropriate amount of Versicol WN powder to water under agitation for several hours to obtain a clear homogeneous solution. Versicol WN23 (from Allied Colloids) is an acrylic acid-acrylamide copolymer having a molecular weight of 7.5×10$^6$.

A substrate was prepared by extruding a blend of two grades of polyether-ester block copolymer ARNITEL EM 740 and EM630 (from Akzo) with BaSO$_4$, into a tube. The tube was dipped into the first coating composition prepared above and dried at ambient temperature (room temperature) for 40 minutes. Then the tube was dipped in the second coating composition and dried at ambient temperature over night. The coated surface showed very good lubricous effect when contacted with water. Furthermore, the coating had very good wear resistance and abrasion resistance, the coating being strongly retained on the surface even under tough force.

EXAMPLE 2

In the same manner as in Example 1, a first coating composition was prepared using the following ingredients:

| | |
|---|---|
| U21X: | 250 ml |
| Water: | 100 ml |
| NeoCryl CX 100: | 10 ml |

U21X (from B. F. Goodrich) is a polyester-based, aliphatic polyurethane dispersion containing carboxylic acid groups as internal emulsifier and being stabilized by TEA. The dispersion has a solids content of about 30%, a pH of 8.5 and a viscosity of 75 cps. The dispersion includes 8.3% N-methylpyrrolidone as cosolvent.

A second coating composition as follows was prepared in the same manner as in Example 1:

1.2% Versicol WN23 aqueous solution

A balloon catheter having a poly(ethylene terephthalate) (PET) balloon was coated with the above coating compositions in the following manner. The PET balloon was inflated and coated with the first coating composition by dipping and dried at ambient temperature for 30 minutes. Then the balloon was dipped in the second coating composition and dried at ambient temperature over night. The resultant dried coating was sterilized by electron beams at a dose of 2×25 KGray.

The obtained coating showed excellent slipperiness and lubricity when contacted with saline. The wear resistance and the abrasion resistance of the coating was also excellent.

EXAMPLE 3

A first coating composition was prepared as described in Example 1 using the following ingredients:

| | |
|---|---|
| Bayhydrol LS-2033: | 250 ml |
| Water: | 250 ml |
| 0.5 Fluorad FC-129 stock solution: | 10 ml |
| 34% NH$_4$OH: | 4 ml |
| NeoCryl CX 100: | 20 ml |

Bayhydrol LS-2033 (from Bayer A. G.) is a water-borne polyurethane which is stabilized by sulfonate groups. The water-borne polyurethane as supplied has a pH of 6.5-7.5, and the sulfonate groups are in sodium salt form. The polyurethane has a solids content of 40%. The dispersion includes no cosolvent.

A second coating composition was prepared as 25 described in Example 1 using the following ingredients:

| | |
|---|---|
| Versicol WN23 solution: Versicol WN23 | 400 ml 1% (w/w) |
| NeoRez R960: | 1.0 ml |

A polyurethane tube (Tecoflex EG-93A, from Themedics, Inc.) was dipped in the first coating composition and dried in an over at 60° C. for 10 minutes. Then the tube was dipped in the second coating composition, dried in an oven at 60° C. for 10 minutes and dipped in the second coating composition once more, after which it was dried at ambient temperature over night. The coating showed excellent slipperiness and lubricity when contacted with water.

EXAMPLE 4

A glass slide was coated using the following coating compositions and the same coating procedures and drying conditions as in Example 1.

First coating composition:

| NeoRez R-940: | 100 ml |
|---|---|
| NeoCryl CX 100: | 4 ml |

NeoRez R-940 (from Zeneca Resins) is a polyether-based, aromatic water-borne polyurethane.

Second coating composition:

| 1.2% Versicol WN23 Aqueous solution: | 400 ml |
|---|---|

The coating showed excellent slipperiness and lubricity when contacted with water.

EXAMPLE 5

Using the same coating procedures as described in Example 1, a stainless steel substrate was coated with the following coating compositions.

First coating composition:

| NeoPac E121: | 250 ml |
|---|---|
| Water: | 100 ml |
| 34% NH$_4$OH: | 2 ml |
| NeoCryl CX 100: | 16 ml |

Second coating composition:

| 1% Versicol WN 23 aqueous solution: | 400 ml |
|---|---|
| First coating composition: | 1.5 ml |

The resulting coating showed excellent slipperiness and lubricity when contacted with water.

EXAMPLE 6

Using the same coating procedures as described in Example 1, a PET substrate was coated with the following coating compositions:

First coating composition:

| Bayhydrol LS 2033: | 200 ml |
|---|---|
| NeoRez R-940: | 100 ml |
| Triethylamine: | 2 ml |
| Water: | 200 ml |
| NeoCryl CX 100: | 10 ml |

Second coating composition:

| 0.8% Versicol WN23 aqueous solution: | 400 ml |
|---|---|

The resulting coating showed excellent slipperiness and lubricity when contacted with water.

EXAMPLE 7

A glass plate was coated with the following coating compositions as described in the following.

First coating composition:

| Sancure 899: | 200 ml |
|---|---|
| NeoPac E121: | 100 ml |
| Acrysol TT-615: (prediluted with equal weight of water) | 1 ml |
| SAG 710: | 1 ml |
| 34% NH$_4$OH: | 4 ml |

Second coating composition:

| 1% Versicol WN23 aqueous solution: | 400 ml |
|---|---|

The first coating composition was brushed onto the glass plate and dried at ambient temperature for 1 hour. Then the second coating composition was sprayed onto the precoated glass surface and dried at ambient temperature over night. The obtained coating showed excellent slipperiness and lubricity when contacted with water.

Acrysol TT-615 is a thickener available from Rohm and Haas Company, and SAG 710 is a defoaming agent available from OSI Specialties, Inc.

EXAMPLE 8

First coating composition:

| Sancure 899: | 250 ml |
|---|---|
| 0.5% Fluorad FC-129 stock solution: | 10 ml |
| 34% NH$_4$OH: | 4 ml |
| Water: | 200 ml |
| Ucarlink XL-29SE: | 40 ml |

Second coating composition:

| 1% Versicol WN23 Aqueous solution: | 400 ml |
|---|---|

A balloon made from polyurethane (Impranil ELN, from Bayer A. G.) was dipped in the first coating composition and dried at ambient temperature for 40 minutes. Then the balloon was dipped in the second coating composition, dried at ambient temperature for 30 minutes and then dipped in the second coating composition once more. The coating was sterilized by EtO (ethylene oxide) sterilization. The coating showed excellent slipperiness and lubricity when contacted with water.

Ucarlink XL-29SE is a polyfunctional carbodimide, available from Union Carbide.

EXAMPLE 9

A PET tube was coated with the following coating compositions as described in the following.

First coating composition:

| NeoPac E121: | 250 ml |
|---|---|
| Water: | 250 ml |
| Ucarlink XL-29SE | 40 ml |

Second coating composition:

| | |
|---|---|
| 1% Versicol WN 23 aqueous solution: | 400 ml |
| First coating composition: | 1 ml |

The PET tube was dipped in the first coating composition and air dried for 30 minutes. Then the precoated tube was dipped in the second coating composition and air dried for 30 minutes followed by drying at 60° C. for 24 hours. The coating showed excellent slipperiness and abrasion resistance when contacted with water.

In the foregoing the invention has been described by means of specific embodiments, but it will be understood that various changes and modifications may be performed without deviating from the scope and spirit of the invention.

NeoRez R-981; NeoRez R-940; NeoRez R-961; NeoRez R-972; NeoRez R-976; NeoRez R-973; NeoPac E-106; NeoPac E-130; NeoPac E-121; NeoCryl CX-100; Fluorad FC-129; U21; U21X; Versicol WN23; Bayhydrol LS-2033; Bayhydrol LS-2100; Bayhydrol LS-2952; Bayhydrol LS-2990; Sancure 899; Sancure 2710; Sancure 1601; Sancure 2026; Ucarlink XL-29SE; Acrysol TT-615 and SAG 710 are trademarks which may be registered in one or more of the designated countries.

I claim:

1. A method of providing a substrate, with a hydrophilic coating which becomes lubricous when contacted with an aqueous fluid, said method comprising:
   a) coating said substrate with a first aqueous coating composition comprising an aqueous dispersion or emulsion of a polymer having organic acid functional groups and an excess of a polyfunctional cross-linking agent having functional groups being capable of reacting with organic acid groups, and drying said first coating composition to obtain a substantially water-insoluble coating layer still including functional groups being reactive with organic acid groups, and
   b) forming a continuous lubricious surface over said first coating composition by contacting said dried first coating composition with a second aqueous coating composition comprising an aqueous solution or dispersion of a hydrophilic polymer having organic acid functional groups, and drying the combined coatings, to bond the hydrophilic polymer to the polymer of the first coating composition through said excess cross-linking agent.

2. A method according to claim 1, wherein the hydrophilic polymer becomes bonded to the polymer of the first coating composition through covalent bonding.

3. A method according to claim 1, wherein the organic acid functional groups are selected from free carboxylic or sulfonic acid groups, metal salts of such acid groups, including alkali metal salts, and quaternary amine salts of such acid groups.

4. A method according to claim 1, wherein the polyfunctional crosslinking agent is selected from polyfunctional aziridines, polyfunctional carboimides and combinations thereof.

5. A method according to claim 1, wherein the polyfunctional crosslinking agent is a crosslinking agent having more than two functional groups per molecule.

6. A method according to claim 1, wherein the polymer in the first coating composition is selected from homo- and copolymers having organic acid functional groups in their structure in an amount sufficient to react with said polyfunctional cross-linking agent.

7. A method according to claim 1, wherein the polymer in the first coating composition is selected from the group consisting of polyurethanes, polyacrylates, polymethacrylates, polyisocrotonates, epoxy resins, acrylate-urethane copolymers and combinations thereof.

8. A method according to claim 7, wherein the polymer in the first coating composition is an acrylate-urethane copolymer and/or a polyurethane.

9. A method according to claim 1, wherein the hydrophilic polymer comprises monomer units from at least one monomer having organic acid functional groups.

10. A method according to claim 9, wherein the hydrophilic polymer is selected from the group consisting of copolymers of acrylic acid, methacrylic acid, isocrotonic acid and combinations thereof.

11. A method according to claim 9, wherein said hydrophilic polymer is formed from monomer units without any organic acid functional groups.

12. A method according to claim 9, wherein the hydrophilic polymer comprises an acrylamide-acrylic acid copolymer.

13. A method according to claim 1, wherein the hydrophilic polymer in the second coating composition has a molecular weight in the range from about 100,000 to about 15 million.

14. A method according to claim 13, wherein the hydrophilic polymer in the second coating composition has a molecular weight in the range of from about 150,000 to about 10 million.

15. A method according to claim 14, wherein the hydrophilic polymer in the second coating composition has a molecular weight in the range of from about 400,000 to about 10 million.

16. A method according to claim 1, wherein the concentration of the hydrophilic polymer in the second coating composition is from about 0.1 to about 5% by weight solids content.

17. A method according to claim 16, wherein the concentration of the hydrophilic polymer in the second coating composition is from about 0.5 to about 3% by weight solids content.

18. A method according to claim 1, wherein the concentration of the polymer in the first coating composition is from about 2 to about 60% by weight solids content.

19. A method according to claim 1, wherein the concentration of the polymer in the first coating composition is from about 5 to about 40% by weight solids content.

20. A method according to claim 1, wherein the concentration of the crosslinking agent in the first coating composition is in the range from about 0.2 to about 30% by weight.

21. A method according to claim 1, wherein the functional groups of the crosslinking agent react with the organic acid functional groups of the polymer in the first coating composition and the hydrophilic polymer in the second coating composition at a temperature below 120° C.

22. A method according to claim 21, wherein the functional groups of the crosslinking agent react with the organic acid functional groups of the polymer in the first coating composition and the hydrophilic polymer in the second coating composition at a temperature in a range of 10°–70° C.

23. The method of claim 1, wherein the substrate is a medical device.

24. The method of claim 1, wherein the substrate is an implantable medical device.

25. The method of claim 1, wherein the substrate is a catheter.

26. The method of claim 1, wherein the substrate is an angioplasty balloon catheter.

27. The method of claim 1, wherein the substrate is a biopsy catheter.

* * * * *